(12) United States Patent
Hwang et al.

(10) Patent No.: US 12,678,248 B2
(45) Date of Patent: Jul. 14, 2026

(54) MEDICAL ROBOT HAVING MULTIPLE MANIPULATION MEANS AND METHODS OF USE THEREOF

(71) Applicant: Canon U.S.A., Inc., Melville, NY (US)

(72) Inventors: Charles George Hwang, Wellesley, MA (US); Takahisa Kato, Brookline, MA (US); Brian Ninni, Woburn, MA (US); Zachary Hamilton Haubert, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 929 days.

(21) Appl. No.: 18/050,776

(22) Filed: Oct. 28, 2022

(65) Prior Publication Data

US 2023/0137954 A1 May 4, 2023

Related U.S. Application Data

(60) Provisional application No. 63/273,753, filed on Oct. 29, 2021.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/30* (2016.02); *A61B 34/71* (2016.02); *A61M 25/0147* (2013.01); *A61B 2017/00477* (2013.01); *A61B 2034/301* (2016.02); *A61B 34/76* (2016.02); *A61B 2090/065* (2016.02); *A61B 90/361* (2016.02); *A61B 90/50* (2016.02)

(58) Field of Classification Search
CPC ... A61B 2034/301; A61B 34/30; A61B 34/71; A61B 1/0051; A61B 1/0057; A61B 34/10; A61B 34/20; A61B 34/37; A61B 1/0016; A61B 34/76; A61B 90/361; A61B 90/50; A61B 2017/00477; A61B 2090/065; A61M 25/0147; A61M 25/0113
See application file for complete search history.

(56) References Cited

U.S. PATENT DOCUMENTS 2,975,785 A    3/1961  Sheldon
3,253,524 A    5/1966  Ashizawa
        (Continued)

FOREIGN PATENT DOCUMENTS

JP       H0337035 A    2/1991
JP       H08215205 A    8/1996
        (Continued)

OTHER PUBLICATIONS

Berthet-Rayne, P. et al., "The i2Snake Robotic Platform for Endoscopic Surgery", Ann Biomed Eng. Oct. 2018, pp. 1663-1675, vol. 46, No. 10.

(Continued)

*Primary Examiner* — Wesley G Harris
(74) *Attorney, Agent, or Firm* — Canon U.S.A., Inc., IP Division

(57) ABSTRACT

An articulated medical device having a hollow core, capable of large degrees of maneuverability through small cavities to reach a target with minimal invasiveness, wherein the medical device is capable of manual and robotic manipulation.

19 Claims, 6 Drawing Sheets

(51) Int. Cl.

| | |
|---|---|
| *A61B 34/30* | (2016.01) |
| *A61M 25/01* | (2006.01) |
| *A61B 17/00* | (2006.01) |
| *A61B 90/00* | (2016.01) |
| *A61B 90/50* | (2016.01) |

(56) References Cited

U.S. PATENT DOCUMENTS

| | | | |
|---|---|---|---|
| 3,610,231 | A | 10/1971 | Takahashi |
| 3,788,303 | A | 1/1974 | Hall |
| 4,207,873 | A | 6/1980 | Kruy |
| 5,355,871 | A | 10/1994 | Hurley |
| 8,317,744 | B2 | 11/2012 | Kirschenman |
| 9,737,373 | B2 | 8/2017 | Schuh |
| 9,839,481 | B2 | 12/2017 | Blumenkranz |
| 10,194,906 | B2 | 2/2019 | Auld |
| 10,470,831 | B2 | 11/2019 | Cohen |
| 10,881,280 | B2 | 1/2021 | Baez, Jr. |
| 2002/0133077 | A1 | 9/2002 | Edwardsen |
| 2005/0197536 | A1* | 9/2005 | Banik .................. A61B 1/0016 600/179 |
| 2005/0216033 | A1* | 9/2005 | Lee .................... A61B 17/0483 606/1 |
| 2007/0135803 | A1 | 6/2007 | Belson |
| 2009/0171151 | A1 | 7/2009 | Choset |
| 2010/0041949 | A1 | 2/2010 | Tolkowsky |
| 2010/0249506 | A1* | 9/2010 | Prisco .................. A61B 1/0051 600/117 |
| 2011/0105954 | A1 | 5/2011 | Cohen |
| 2012/0078053 | A1 | 3/2012 | Phee |
| 2013/0172814 | A1 | 7/2013 | Olson |
| 2014/0222023 | A1 | 8/2014 | Kim |
| 2016/0067450 | A1 | 3/2016 | Kowshik |
| 2016/0338782 | A1 | 11/2016 | Bowling |
| 2018/0049794 | A1 | 2/2018 | Swayze |
| 2018/0049795 | A1 | 2/2018 | Swayze |
| 2019/0105468 | A1* | 4/2019 | Kato ..................... A61B 10/06 |
| 2019/0261830 | A1 | 8/2019 | Banik |
| 2020/0060516 | A1 | 2/2020 | Baez, Jr. |
| 2020/0253669 | A1 | 8/2020 | Diolaiti et al. |
| 2020/0297442 | A1 | 9/2020 | Adebar et al. |
| 2021/0259794 | A1 | 8/2021 | Kato et al. |

FOREIGN PATENT DOCUMENTS

| | | | |
|---|---|---|---|
| JP | H10262900 A | 10/1998 | |
| JP | 2005237964 A | 9/2005 | |
| JP | 2009018116 A | 1/2009 | |
| JP | 20100279688 A | 12/2010 | |
| WO | 2009069394 A1 | 6/2009 | |
| WO | 2012046605 A1 | 4/2012 | |
| WO | WO-2016061431 A1 * | 4/2016 | ......... A61B 1/00078 |
| WO | WO-2016164311 A1 * | 10/2016 | ........... G06T 7/0012 |
| WO | WO-2017044874 A1 * | 3/2017 | ............. A61B 1/009 |
| WO | WO-2020176400 A1 * | 9/2020 | ............. A61B 34/20 |

OTHER PUBLICATIONS

Rozeboom, E.D., "Feasability of joystick guided colonoscopy", J Robotic Surg. 2015, pp. 173-178, No. 9.

Mangels, D.R., et al., Robotic-assisted Percuaneous Coronary Intervention, Catheter Cardiovasc. Interv., Jul. 19, 2017, pp. 948-955, Wiley Periodicals, Inc.

\* cited by examiner

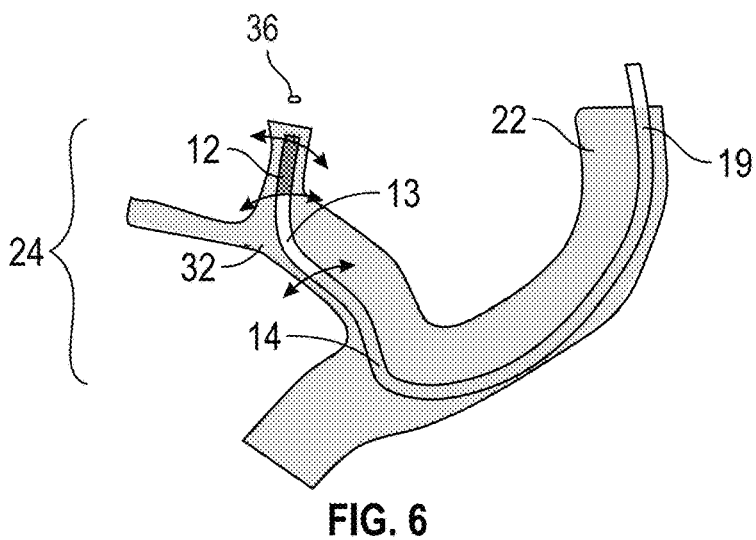

FIG. 6

| Workflow 1: detachable actuation unit |
| --- |

| Move the catheter insertion stage into the vertical catheter loading position |
| --- |

| Remove catheter from packaging, leaving the straight packaging tube on |
| --- |

| Attach camera to actuation unit |
| --- |

| Complete camera functional check |
| --- |

| Complete catheter function check |
| --- |

| Move catheter insertion stage into approximate position |
| --- |

| Remove the straight packaging tube |
| --- |

| Detach actuation unit from catheter insertion stage |
| --- |

| Manually insert catheter to the first carina |
| --- |

| Adjust position of catheter insertion stage |
| --- |

| Attach actuation unit to the support platform |
| --- |

| Enter robot mode and use controller to navigate to lesion(s) |
| --- |

FIG. 7

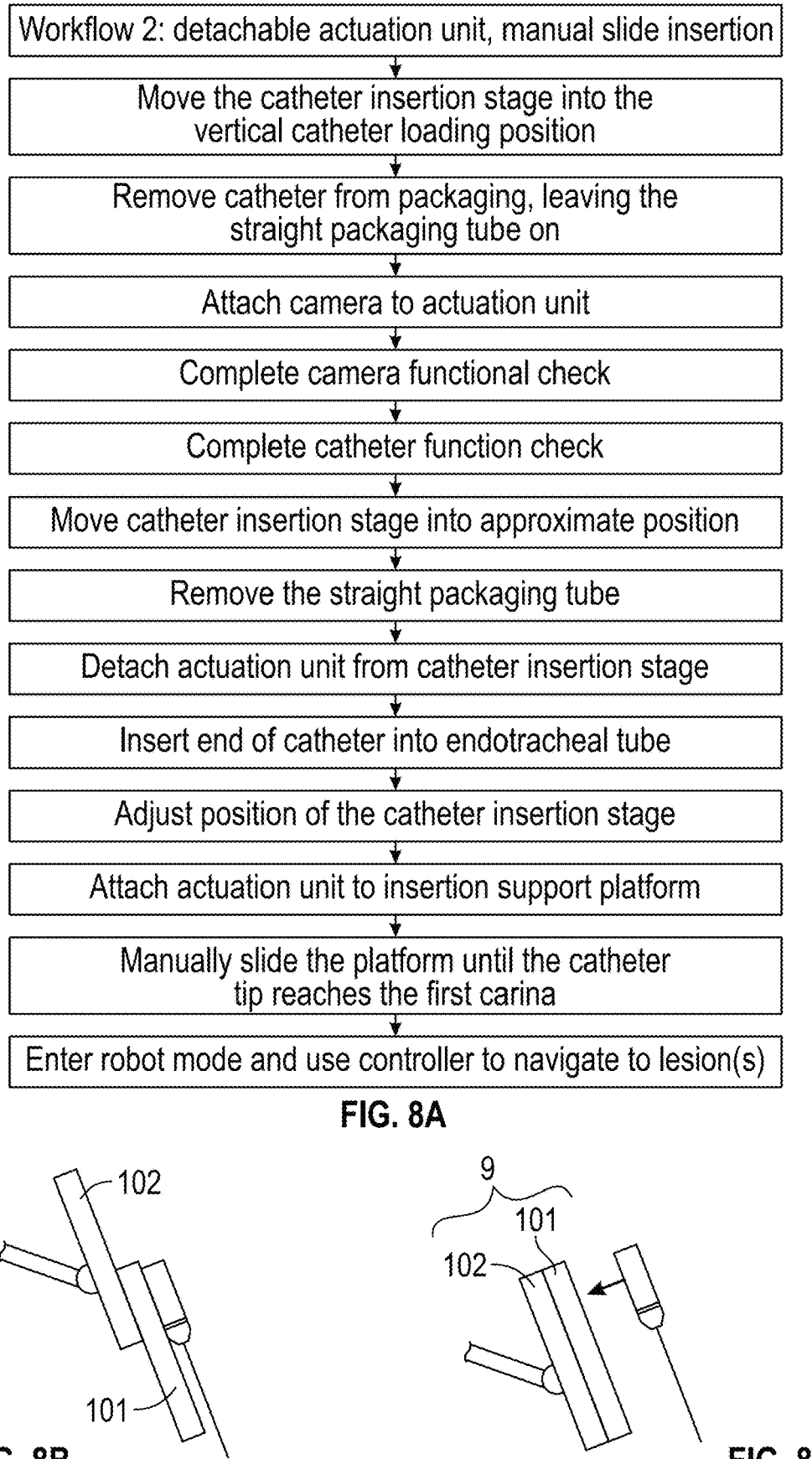

Workflow 2: detachable actuation unit, manual slide insertion

Move the catheter insertion stage into the vertical catheter loading position

Remove catheter from packaging, leaving the straight packaging tube on

Attach camera to actuation unit

Complete camera functional check

Complete catheter function check

Move catheter insertion stage into approximate position

Remove the straight packaging tube

Detach actuation unit from catheter insertion stage

Insert end of catheter into endotracheal tube

Adjust position of the catheter insertion stage

Attach actuation unit to insertion support platform

Manually slide the platform until the catheter tip reaches the first carina

Enter robot mode and use controller to navigate to lesion(s)

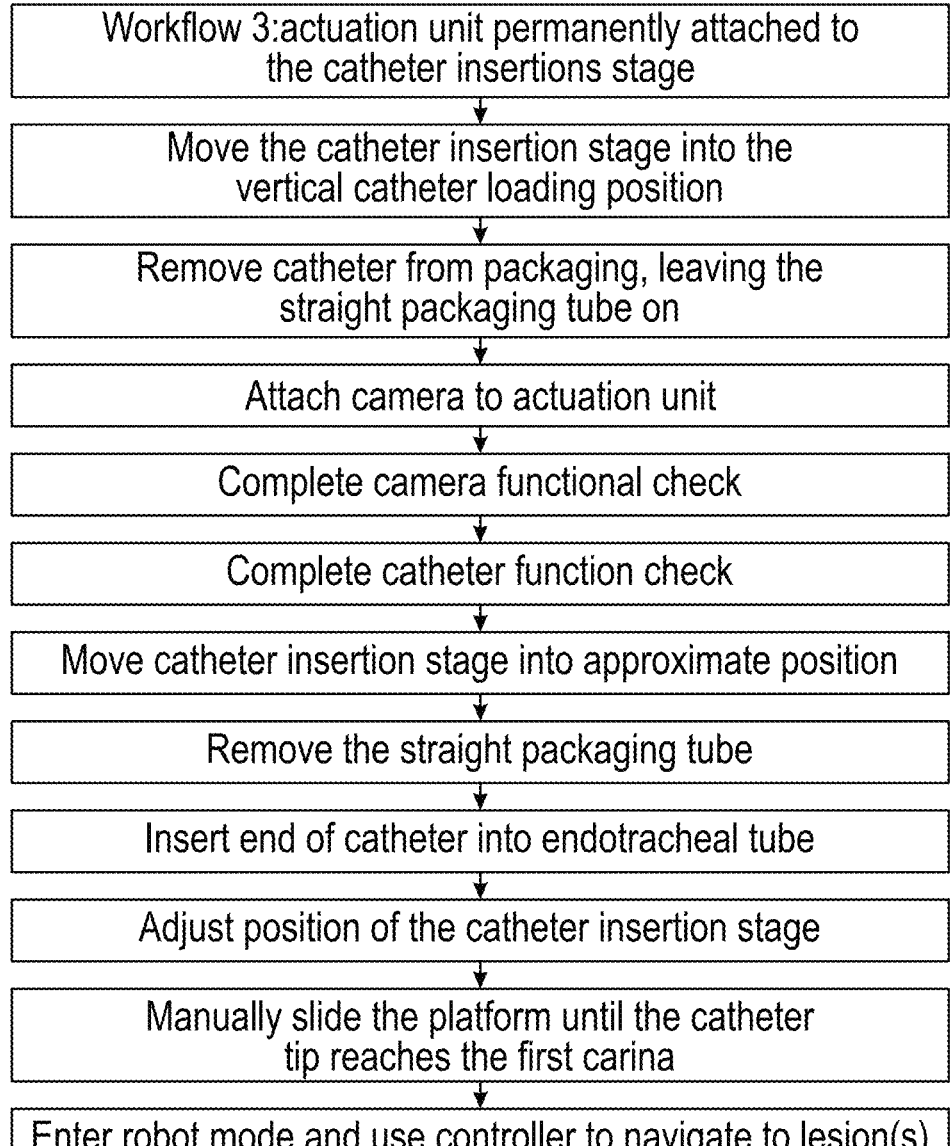

Workflow 3:actuation unit permanently attached to the catheter insertions stage

↓

Move the catheter insertion stage into the vertical catheter loading position

↓

Remove catheter from packaging, leaving the straight packaging tube on

↓

Attach camera to actuation unit

↓

Complete camera functional check

↓

Complete catheter function check

↓

Move catheter insertion stage into approximate position

↓

Remove the straight packaging tube

↓

Insert end of catheter into endotracheal tube

↓

Adjust position of the catheter insertion stage

↓

Manually slide the platform until the catheter tip reaches the first carina

↓

Enter robot mode and use controller to navigate to lesion(s)

FIG. 9A

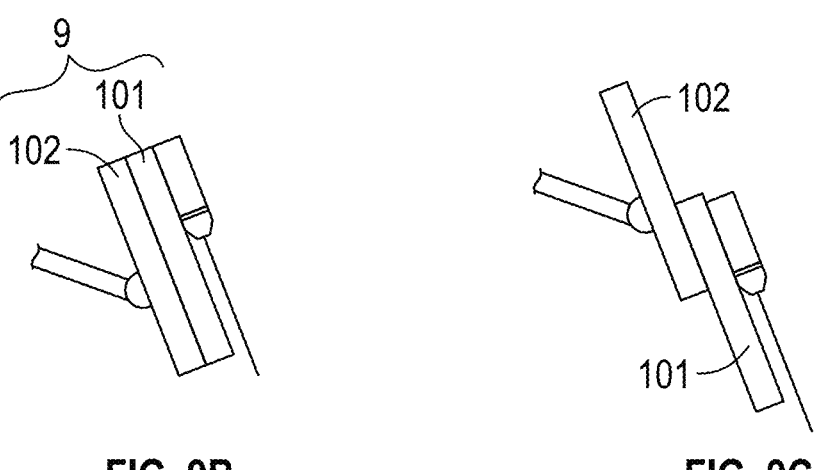

FIG. 9B             FIG. 9C

MEDICAL ROBOT HAVING MULTIPLE MANIPULATION MEANS AND METHODS OF USE THEREOF

CROSS REFERENCE TO RELATED PATENT APPLICATIONS

This application claims priority from U.S. Provisional Patent Application No. 63/273,753, filed on Oct. 29, 2021, in the United States Patent and Trademark Office, the disclosure of which is incorporated by reference herein, in its entirety.

FIELD OF THE DISCLOSURE

The present disclosure relates generally to apparatus and methods for medical application. More particularly, the subject disclosure is directed to an articulated medical device having a hollow cavity for allowing a medical tool to be guided through the hollow cavity for medical procedures, including endoscopes, cameras, and catheters.

BACKGROUND OF THE DISCLOSURE

Bendable medical instruments such as endoscopic surgical instruments and catheters are well known and continue to gain acceptance in the medical field. The bendable medical instrument generally includes a flexible body commonly referred to as a sleeves or sheaths. One or more tool channels extend along (typically inside) the flexible body to allow access to a target located at a distal end of the body.

The instrument is intended to provide flexible access within a patient, with at least one curve or more leading to the intended target, while retaining torsional and longitudinal rigidity so that a physician can control the tool located at the distal end of the medical instrument by maneuvering the proximal end of the instrument.

Recently, to enhance maneuverability at the distal end of the instrument, robotized instruments that control distal portions have emerged. In those robotized instruments, to create curves locally at the distal portion by robotics, different techniques have been disclosed.

By way of example, United States patent publication number 2016/0067450, provides multiple conduits to retain the shape of the proximal part, while the driving tendons are bending the distal part in the medical instruments. The multiple conduits would be controlled selectively in a binary way by constraining or unconstraining the proximal ends of the conduits. By selecting the constrained conduits, the bendable medical device can change the length of bending distal segment by changing the stiffness of the bendable medical device based on the area where the conduits deploy.

Furthermore, these robotically controlled instruments typically require a stationary support or base from which the robotic instrument can be inserted into the patient. As space within an operating room become more constricted with personnel and instrument, there is a need in the industry to minimize the size of stationary support necessary to advance the catheter into the body of the patient. A smaller support means lighter weight and potentially lower cost, as well.

Various examples of supports for the robotic instruments can be seen in United States patent publication number 2020/0253669 to Diolaiti, as well as United States patent publication number 2020/0297442 to Adebar. However these examples are large and cumbersome and require a lengthy amount of time for set-up, use, and manipulation, if necessary.

SUMMARY

Thus, to address such exemplary needs in the industry, the present disclosure provides a method for manipulating a medical apparatus comprising the steps of: providing the medical apparatus comprising: a bendable body having at least one bendable section; at least one control wire slideably situated in the bendable body and attached to a distal end of the bendable body; and an actuator connected to the at least one control wire and configured to actuate the control wire to manipulate the at least one bendable section, followed by manipulating the medical apparatus manually; providing a supporting insertion unit configured to removably couple with the medical apparatus, wherein the supporting insertion unit is configured for manual or robotic manipulation; manipulating the medical apparatus manually, while configured on the supporting insertion unit; and manipulating the medical apparatus robotically, wherein the manual manipulation of the medical device while configured on the supporting insertion unit is guided by the supporting insertion unit.

In various embodiments, the method further comprising a controller in communication with the medical device, configured to robotically manipulate the at least one control wire.

In yet additional embodiments, the method details the controller manipulates the medical apparatus robotically.

It is further contemplated that the actuator is configured for manual manipulation of the medical apparatus, when disconnected from the supporting insertion unit.

In yet another embodiment, the actuation unit is configured to be held by an end user when the bendable body assembly is detached from the supporting insertion unit.

In further embodiment, the supporting insertion unit further comprises at least one force sensor to measure a force applied to the bendable body.

In other embodiment of the method a second bendable section, wherein a controller is configured to control one bending section directly associated with an end user input, and to control the second bending section associated with an algorithm in the controller.

In additional embodiment, the controller controls the most distal bendable section directly associated with an end user input, and controls the other bendable section with an algorithm in the control mode.

In addition, the method further comprises connecting the medical apparatus to the supporting insertion unit for robotic manipulation of the medical apparatus.

It is further contemplated that the medical apparatus further comprises a tool channel parallel to a length of the medical apparatus. In addition, the tool channel is configured to accommodate a biopsy tool, a camera, or the like.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

FIG. 6 depicts a cut-away view of an exemplary bendable medical device navigating through a tortuous pathway, according to one or more embodiment of the subject apparatus, method or system.

FIG. 7 provides a flow chart detailing a method for employing an exemplary bendable medical device, according to one or more embodiment of the subject apparatus, method or system.

FIG. 8A provides a flow chart detailing a method for employing an exemplary bendable medical device, according to one or more embodiment of the subject apparatus, method or system.

FIGS. 8B and 8C are side perspective views of an exemplary bendable medical device at various attachment orientations, according to one or more embodiment of the subject apparatus, method or system.

FIG. 9A provides a flow chart detailing a method for employing an exemplary bendable medical device, according to one or more embodiment of the subject apparatus, method or system.

FIGS. 9B and 9C are side perspective views of an exemplary bendable medical device at various attachment orientations, according to one or more embodiment of the subject apparatus, method or system.

Figure 1:
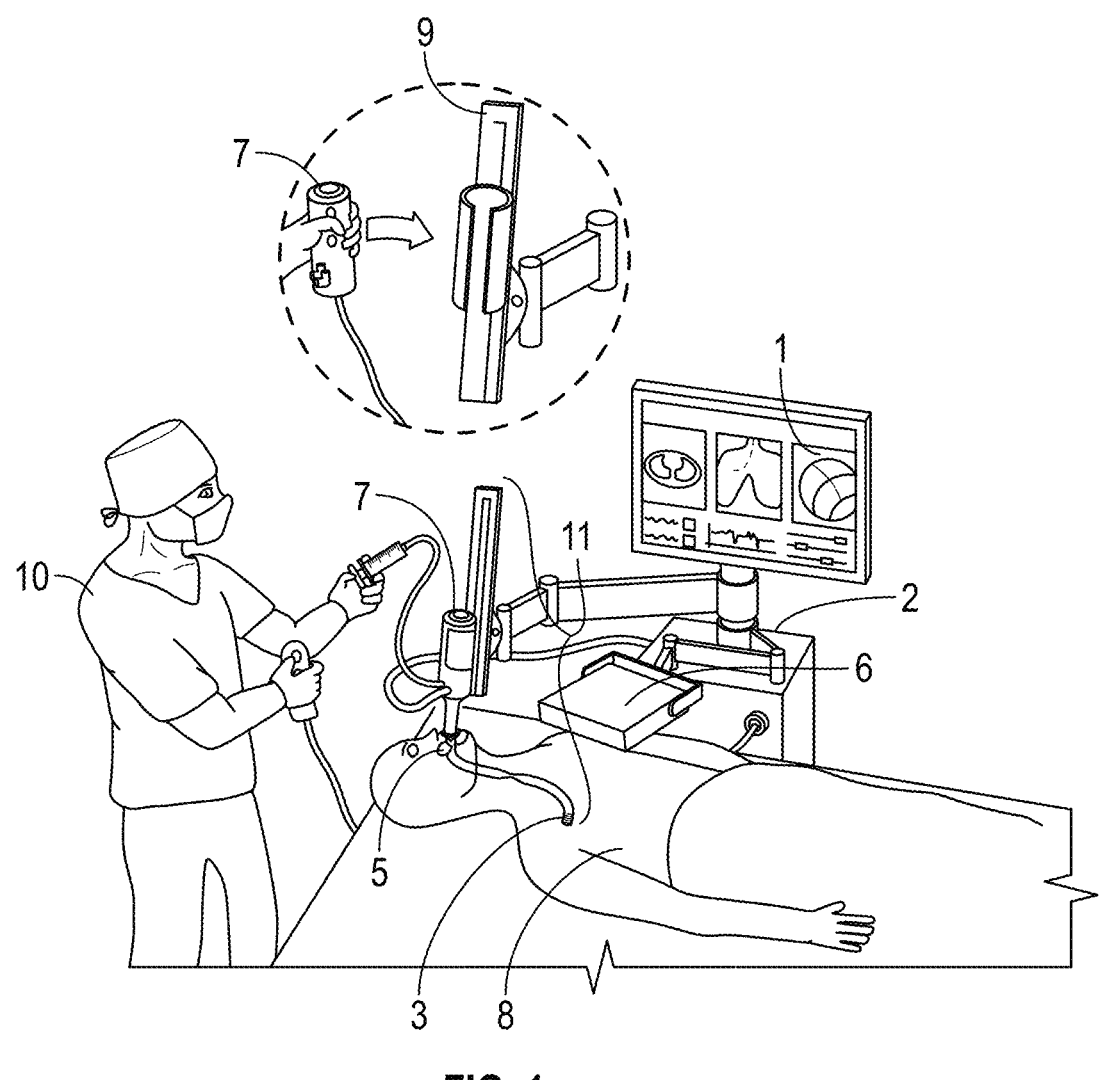
FIG. 1 illustrates an exemplary bendable medical device incorporating various ancillary components, according to one or more embodiment of the subject apparatus, method or system.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

FIG. 1 illustrates an exemplary bendable medical device 11 incorporating various ancillary components, according to one or more embodiment of the subject apparatus, method or system. The bendable medical device 11 is in communication with navigation software on a computer 1, as well as a controller 2 which are communicatively-coupled via a bus to transmit/receive data between each other. Moreover, the navigation software and computer 1 are connected to and communicates with a CT scanner, a fluoroscope and an image server (not in Figure), which are external of the bendable medical device 11. The image server includes but is not limited to a DISCOM™ server connected to a medical imaging device 11 including but not limited to a CT and/or MRI scanner and a fluoroscope. The navigation software 1 processes data provided by the controller 2 and data provided by images stored on the image server, and/or images from the CT scanner and the fluoroscope in order to display images onto the image display.

The images from the CT scanner are pre-operatively provided to the navigation software 1. With the navigation software 1, an end user may create an anatomical computer model from the images. In this particular embodiment, the anatomy examined are the lungs. From the chest images of the CT scanner, the clinical user can segment the lung airways for various clinical treatments, such as a biopsy. After generating the lung airway map, the user can also create a plan for accessing the lesion for the biopsy. The plan includes the pathway for insertion of the bendable body 3 of the bendable medical device 11, through the airways to arrive at the lesion. The controller 2 includes a control circuitry, which is communicatively-coupled with the actuation unit 7 (also referred to herein as 'actuator'), supporting insertion unit 9, field generator 6 and man-machine interface 21 (see FIG. 2B) for manipulating those instruments.

The bendable body 3 is attached with the actuation unit 7 and forms the bendable medical device 11. The actuation unit 7 is configured to bend various bending sections of the bendable body 3 with the controller 2.

The bendable medical device 11 is detachably attached to the supporting insertion unit 9, thus allowing for the bendable medical device 11 to be stationary. The controller 2 is configured to synchronize the behavior/motion of actuation unit 7 with the behavior of supporting insertion unit 9, and can change those behaviors based on whether the bendable medical device 11 is attached to the supporting insertion unit 9 (hereafter "on-state") or detached from the supporting insertion unit 9 (hereafter "off-state").

In this subject example, the bendable body 3 is configured to be inserted into the lungs of a patient 8. In an exemplary embodiment, the physician 10 will facility the input value(s) to the controller 2, via the man-machine interface 21 (e.g. Joystick), and the controller 2 will move the actuation unit 7 and/or supporting insertion unit 9 to reflect the physician's 10 intended movements of the bendable body 3 into the patient 8. The bendable body 3 advances to the target lesion, where a medical tool (e.g. Biopsy tool) may be guided to the lesion by using tool channel in the bendable body 3.

Figure 2A:
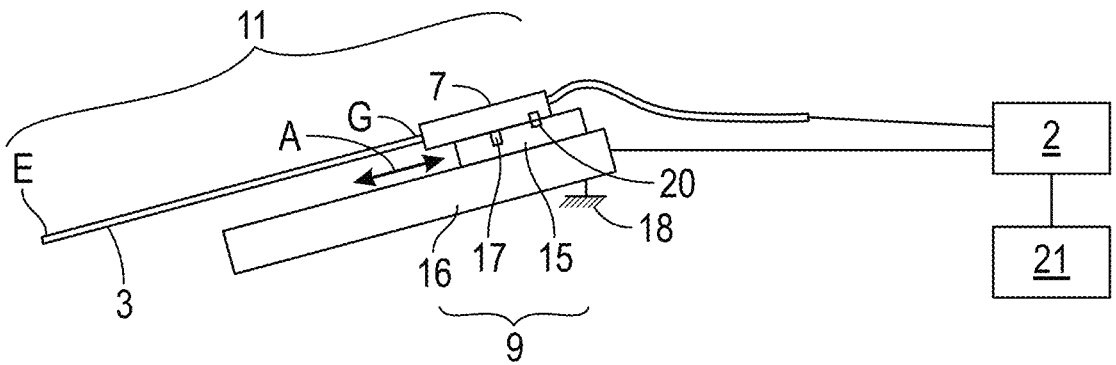
FIG. 2A provides a partial depiction of an exemplary bendable medical device, with the device mounted to a supporting insertion unit, according to one or more embodiment of the subject apparatus, method or system.
Figure 2B:
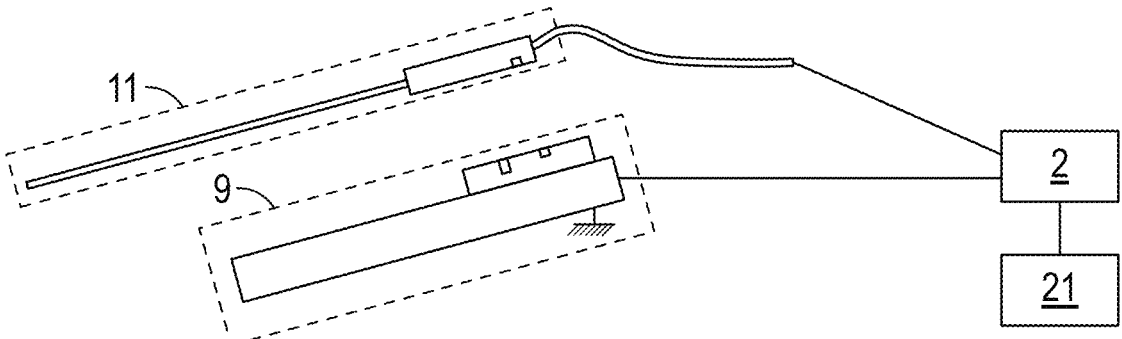
FIG. 2B provides a partial depiction of an exemplary bendable medical device, with the device separated from the supporting insertion unit, according to one or more embodiment of the subject apparatus, method or system.

FIGS. 2A and 2B illustrate the two configurations of the bendable medical device 11, namely, on-state (FIG. 2A) and off-state (FIG. 2B). In the on-state configuration, the bendable medical device 11 is mounted and locked on the supporting insertion unit 9 with a detachable lock 20. The lock 20 may be unlocked manually with a mechanical unlock structure or with an electrical unlock structure incorporating the controller 2. An attachment sensor 17 may be configured on the supporting insertion unit 9 and/or bendable body 3, to detect whether the bendable body assembly 11 is in the on or off state. An insertion slider 15, moving along line A, may be used to guide the bendable body 3 based on the command from the controller 2. The bendable body 3 has a distal end and a proximal end, represented by E and G, respectively in FIG. 2A.

In the on-state configuration, the physician 10 will control the insertion slider 15 and/or bendable body 3 with the man-machine interface 21, and the bendable body 3 will advance into the patient robotically.

In the off-state configuration, provided in FIG. 2B, the bendable medical device 11 is detached from insertion slider 15 and supporting insertion unit 9 all together. In this configuration, the physician 10 retains the actuation unit 7 with his/her hand(s), and can manipulate the bendable body 3 with either the man-machine interface 21 via controller 2, or can manually manipulate the bendable body 3.

This ability to switch from the on-state configuration to the off-state configuration, and vise-versa, allows for flexible adaptation of the bendable medical device 11, depending on the needed circumstances. For instance, during initial advancement of the bendable medical device 11 through larger/wider portions of a patient's anatomy, the off-state configuration can been implemented to encourage rapid advancement of the bendable medical device 11, thus saving time. Once the bendable medical device 11 reaches more tortuous sections of the patient's anatomy, the bendable medical device 11 may be switched to the on-state configuration, allowing for more finite advancement of the bendable medical device 11, which are done at a slower deliberate pace so as to ensure minimal abrasion and discomfort to the patient.

As detailed above, the subject method of use of the medical device 11 allows the physician 10 to use the bendable body assembly 11 both with and without the supporting insertion unit 9. Robotic insertion control with the supporting insertion unit 9 can provide a user with precise and consistent controls of insertion and bending motion of the bendable body by synchronizing the insertion and bending motions with the control of the bendable body assembly with the supporting insertion unit 9. Besides, the control of the bendable body assembly 11 without the supporting insertion unit 9 can provide a user (physician 10) with agile and flexible insertion operation while the user continues to leverage the robotic bending control, which significantly enhances safety and flexibility in advancing and retracting the medical device.

The physician 10 is provided tactile feedback regarding the insertion of the bendable body so that the physician 10 can adjust insertion speed and force intuitively and quickly, as would be expected in the conventional manual insertion practice. However, the duration time for the procedure can be shortened while maintaining the same level of safety as the conventional manual insertion methods. The present disclosure reduces the insertion length with robotic insertion control, by allowing for manual insertion, the supporting insertion unit 9 can be miniaturized with a shorter stroke, which further reduces cost for manufacture.

Further advantages include using force information in the operation mode when the sheath is detached from the supporting insertion unit, wherein the controller can assist in bending the sheath with control of forces that the sheath would apply to the anatomy, while the user manually perform the insertion. Specifically, this is advantageous when the user controls a part of the degrees of freedom of motion in the sheath among the many degrees of freedom of motion to control.

By controlling the most distal bending section directly with the controller, the user can maintain the same maneuvers for the procedure as the conventional endoscope's. Also, since the controller can assist the rest of the degree of the freedom, the user can leverage additional degree of the freedom to improve the dexterity with the simple and minimal control parameters.

Figure 3:
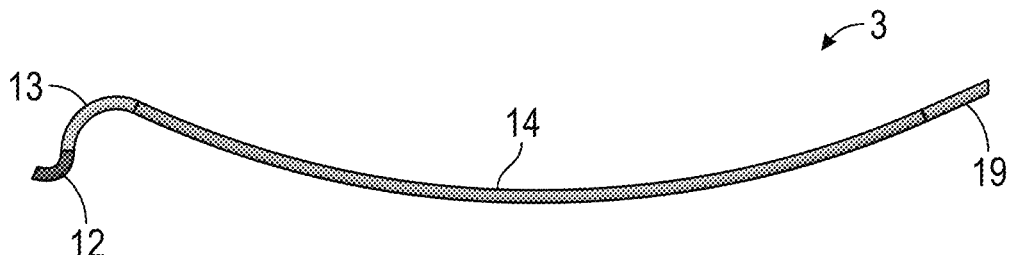
FIG. 3 depicts a perspective view of an exemplary bendable medical device, according to one or more embodiment of the subject apparatus, method or system.

FIG. 3 is a schematic drawing to explain the bendable segments of the bendable medical device 3. The bendable medical device 3 comprises a proximal part 19 and three bendable segments, which are the first, second, and third bendable segments 12, 13, 14, respectively. The bendable segments 12, 13, 14, can independently bend and can form a shape with three independent curvatures, with each of the bendable segment, 12, 13 and 14, capable of independent manipulation in all three axes.

Figure 4:
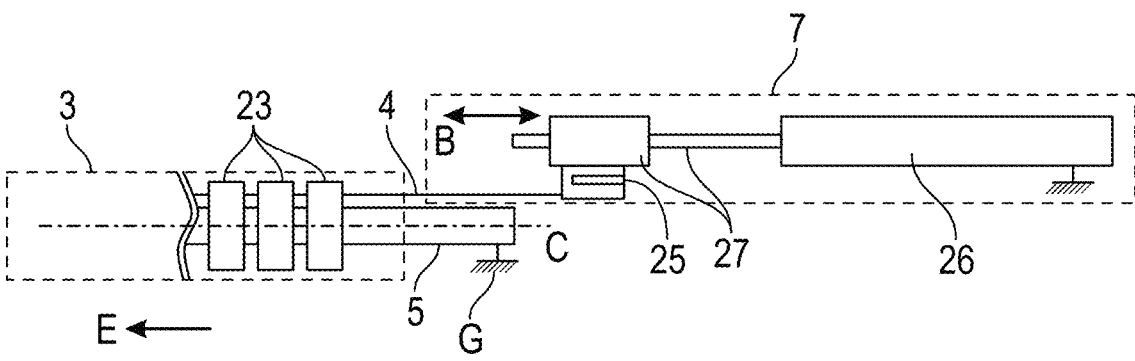
FIG. 4 provides an internal view of an exemplary bendable medical device, according to one or more embodiment of the subject apparatus, method or system.

FIG. 4 explains the bending principles of the bendable medical device 11, incorporating one or more driving wire (s) 4. The actuation unit 7 comprises motor 26, linear motion structure 27, and a force sensor 25. The motor 26 is configured to move the liner motion structure 27 to create linear motion along line B, both fore and aft. The force sensor 25 is also attached to the actuation unit 7, and will be moved together with the linear motion structure 27, thus allowing for accurate force readings when the linear motion structure 27 encounters resistance. The driving wire 4 is terminated on the linear motion structure 27, and is pushed and pulled along line B. The opposing end of driving wire 4 is terminated on the distal end of one of the three bending sections 12, 13 or 14, situated slidingly through the wire guides 23. As the linear motion structure 27 is pushed and pulled by the motor 26, the bending section where the end of the driving wire 4 is terminated, is subjected to bending moment and can be bent according to the linear motion structure 27. The force sensor 25 can sense the force applied to driving wire 4, as well as the resistance for further calculations and amendments in force by the motor, if need be.

Figure 5A:
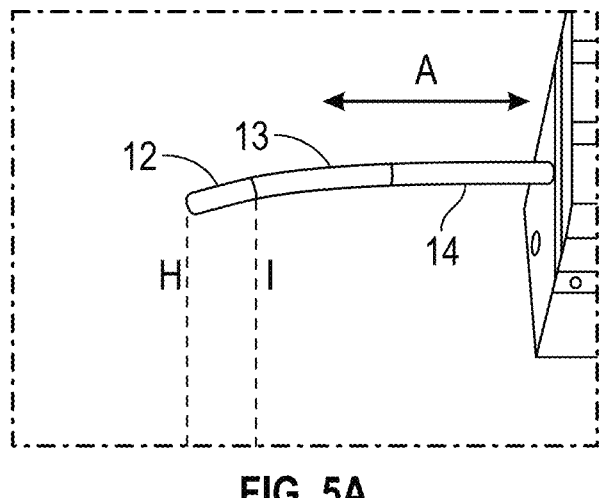
FIGS. 5A-5C provide side perspective views of an exemplary bendable medical device at various bendable orientations, according to one or more embodiment of the subject apparatus, method or system.
Figure 5B:
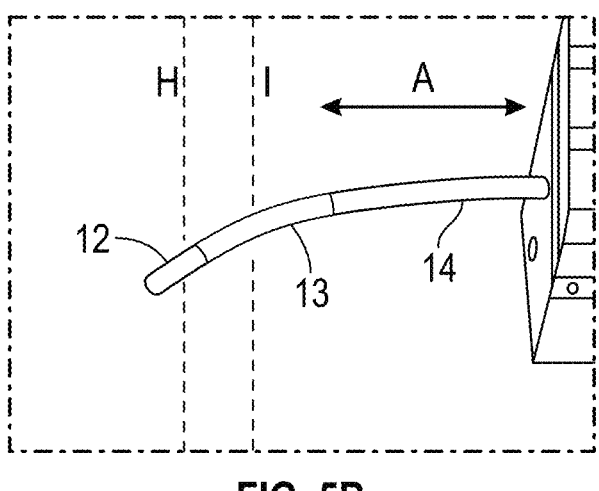
Figure 5C:
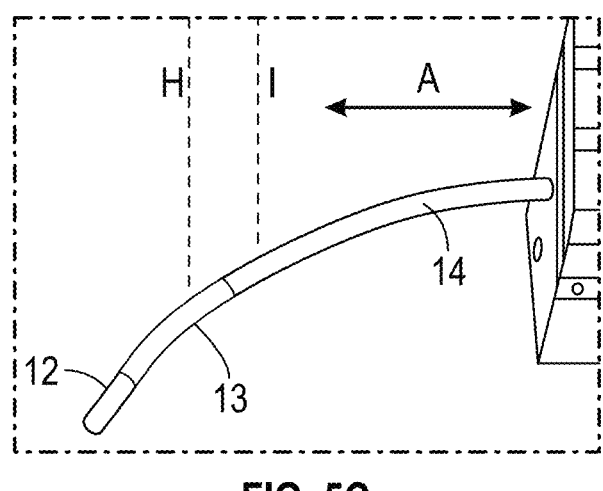

FIGS. 5A-5C detail exemplary embodiments of unique motion of the bendable medical device 11, with three bending sections 12, 13 and 14, and the supporting insertion unit 9, incorporating follow-the-leader (FTL) motion. In the depictions provided, the physician may first issue commands to bend the distal bending section 12 (FIG. 5A). After that, the physician may advance the bendable body 3 with the supporting insertion unit 9 along line A. When the distal part of middle section 13 is advanced to the position of the distal bending section 12 at the moment shown in FIG. 5A (position H-I), the controller 2 is continually and automatically bending the middle section 12 to the same bending angles as the distal bending section 12 at that position, much like follow the leader, to retain precise placement of the bendable body 3 as it is advanced. After that, the physician can advance the bendable body 3 further with the supporting insertion unit 9 along line A (FIG. 5c). Upon advancement, when the distal part of the proximal bending section 14 reaches position H-I, the controller once again also bend the proximal bending section 14 to mimic the bending angles of bending sections 12 and 13, at that position (H-I). Thus with this follow the leader method, the bendable body 3 can advance through tortuous pathways while retaining it's shape and trajectory.

FIG. 6 provides a cut-away view of an exemplary bendable medical device 11 inserted into a cavity, specifically, the peri-bronchial area of the human lung, which is a lateral area surrounding the airways. This area is a known challenge to target as identified in literature, and the prior art, due to the limited distal dexterity of the conventional catheter. To reach the lesion through airways 22 in the navigation stage, the first and the second bendable segments 12, 13, respectively, navigate the bendable medical device 11 through the bifurcation point 32. The first bendable segment 12 can adjust the shape/orientation to the daughter branch while the second bendable segment 13 can adjust the shape/orientation to the parent branch in the bifurcation point 32, as the bendable medical device 11 advances through the bifurcation point 32. Once the first and the second bendable segments 12 and 13 pass the bifurcation point 32, those segments may act as guides for the rest of the bendable medical device 11, so that the insertion force from the proximal end of the bendable medical device 1 can be effectively transformed into the insertion force for a distal part of the bendable medical device 11 without serious prolapsing of the distal section. Once the distal end 34 of the bendable medical device 11 reaches the vicinity of a lesion 36, the bendable medical device 3 would direct the distal end 24 to the lesion 36, which locates the lateral area around the airway, by bending the first and the second bendable segments 12 and 13, respectively. Since the airway doesn't directly connect with the lesion 36, this is one of the more difficult configurations for a conventional catheter.

With the first, the second and the third bendable segments 12, 13 and 14, respectively, the bendable medical device 11 can orient the three bendable segments 12, 13 and 14, without moving the proximal part 19 that goes through all bifurcations to this lesion 36. By using the three-dimensional bending capability of the first and the second bendable segments 12 and 13, the bendable medical device 11 can perform unique maneuvers to enhance capability of peri-bronchial targeting. Therefore, the bendable medical device 11 can provide improved access to the intended lesion 36 through tortuous pathways. Also, the bendable medical device 11 can have different flexibility along the axial direction without increasing the size or number of the jointing points.

In the on-state configuration, the physician 10 issues a command, via the controller 2, to move the bendable body 3 with the actuation unit 7 and supporting insertion unit 9, while the controller 2 further controls the degree freedom of motion in all three bendable segments 12, 13 and 14 of the bendable body 3, automatically. This combination of control creates the useful follow the leader motion when advancing the bendable body 3, with minimal control parameters required from the physician 10, making control and advancement of the bendable medical apparatus, i.e. medical device 11, easy and intuitive.

However, in the off-state configuration, the Physician can also control the bendable body 3 manually. At the same time, the controller 2 can use the force data generated from the force sensor 25 to provide feedback control for the middle and proximal sections, 13 and 14 respectively, such that that bendable body 3 avoids stressing the walls of the lungs.

FIG. 7 is the workflow diagram showing an exemplary transition from manual insertion of the bendable medical device 11 in the off-state configuration to robotic insertion of the bendable medical device 11 in the on-state configuration, incorporating robotic steering.

Firstly, the Physician 10 attaches bendable body 3 to the actuation unit 7. At this time, the bendable body 3 has a tool channel in the body with an endoscope unit in the tool channel for endoscopic view. Concurrently, an anesthesiologist inserts an endobronchial tube (ET tube) into patient 8. The Physician 10 then moves the supporting insertion unit 9 into the vertical catheter loading position, and removes the bendable body 3 from packaging, leaving the straight packaging tube on. The Physician 10 attaches bendable body 3 to the actuation unit 7 and inserts the camera to complete a camera functional test.

The physician 10 then completes catheter function check and moves the supporting insertion unit 9 into an approximate position. The physician 10 then removes the straight packaging tube and detaches the actuation unit 7 from supporting insertion unit 9. Now the physician 10 may manually insert the bendable body 3 into the first carina, and then adjust the position of supporting insertion unit 9 for reattachment of the actuation unit 7 onto an insertion stage 9. At this point, the system enters robot mode (on-state configuration) and the physician 10 uses the supporting insertion unit 9 and the controller to robotically navigate the bendable body 3 to the target.

In a second embodiment detailed below and shown in FIG. 8A, the initial description is identical to first embodiment above, with the workflow differing at the point where the physician 10 inserts the bendable body 3. Specifically, the supporting insertion unit 9 (see FIG. 8B) in this embodiment includes the manual sliding component 101 and a motorized base 102. The manual sliding component 101 is capable of being slidably moved along an insertion direction of the supporting insertion unit 9, wherein the physician 10 may manually slide the slider 101, or the motorized base 102 may be initiated for moving the slider 15. The slider 15 further includes an attachment sensor 17 and lock 20 to detachably accept the catheter assembly. The motorized base 102 is substantially equivalent to the slider 15 and base 16 in embodiment 1, with the exception that the motorized base 102 is slidable with a motor commanded controller.

The manual sliding component 101 can reduce the necessary insertion stroke in motorized base 102 to cover the catheter insertion from patient mouth to peripheral lesion. The shorter stroke further miniaturizes the actuation unit as a whole, which in turn reducing total weight and size of the supporting insertion unit 9 to achieve an even more compact and affordable robotic system. In addition, the manual sliding component 101 could reflect necessary insertion position changes for all steps before robotic insertion from the trachea to target lesion, including attachment of the catheter, fine position adjustment to attach actuation 10 with insertion unit 9 and insertion from ET tube (mouth) to the carina (the first bifurcation of the airways). Furthermore, it is of note, that FIG. 8A only details the workflow of this embodiment up to the steps before robotic advancement/ insertion, which is the transition from manual insertion with robotic steering 28 in off-state configuration to robotic insertion with robotic steering 29 in on-state configuration, with the remaining steps provided below.

Upon successful transition from the off-state configuration to the on-state configuration, the Physician 10 now moves the supporting insertion unit 9 into the vertical catheter loading position to attach the catheter without mechanical interference between the bendable body 3 and surrounding objects. In this position the physician 10 has much better ergonomics to attach the bendable body 3 to the actuation unit 7. Please note than in this step, the actuation unit 7 is mounted on the slider 101. In one embodiment, the slider 101 would locate at the most proximal position to create enough space to accept the full length of bendable body 7 without interruption of to ET tube when the bendable body 3 is attached with actuation unit 7. The Physician 10 then removes the bendable body 3 from packaging, leaving the straight packaging tube on, and attaches the bendable body 3 to the actuation unit 7 on the slider 101. The Physician 10 then inserts camera and completes a camera functional test, as well as a catheter function check.

The physician 10 then moves the supporting insertion unit 9 (assembly of manual sliding component 101 and motorized base 102) into the approximate position. In this step, the physician 10 adjusts the orientation of supporting insertion unit 9 to the angle of ET tube, and adjusts the distance between tip of catheter to ET tube. The physician 10 then removes the straight packaging tube and detaches the actuation unit 7 from the supporting insertion unit 9 (FIG. 8B, Right Top). In this step, the physician 10 holds the actuation unit 7 with the bendable body 3 and manipulates them just like conventional bronchoscope. Then, the physician 10 manually inserts the tip of bendable body 3 into ET tube. In this step, the tip of bendable body 3 remains in an area of ET tube outside of patient's mouth.

The physician 10 proceeds to adjust the orientation of the supporting insertion unit 9. In this step, the tip of bendable body 3 remains in the area of ET tube outside of patient's month. The orientation adjustment between the insertion stage 9 and ET tube would become visible with the bendable body 3 since one end of bendable body 3 (the tip) is held with ET tube, as well as the other end (proximal end) is held with the actuation unit 7 on the insertion stage 9. This visual information allows the physician 10 to adjust the orientation easily and intuitively straighten the bendable body 3.

The physician 10 can now attach the actuation unit 7 to the supporting insertion unit 9. At this time, physician 10 can manually move the slider 101 as needed to absorb position discrepancies. The physician 10 manually slides the slider 101 until catheter reaches the first carina (i.e. similar to December 2020 CINC prototype platform, e.g. FIG. 2A). During this step, physician would not need to meticulously maneuver bendable body 3 with the robotic control with motorized base 102 since the pathway from ET tube to the carina is almost a single track. Therefore, with the slider 101, this step would reduce the stroke of motorized base 102. Once completed, the system may now enter robot mode and use the controller to navigate the bendable body 3 to the target.

In this second exemplary embodiment, the combination of manual sliding with the slider 101 and motorized base 102 movement allow the system to have a minimal stroke of motorized base 102 and reducing the total weight and size for the supporting insertion unit 9. Also, the manual slider 101 would give the physician 10 greater flexibility and ergonomics for the steps involving the supporting insertion unit 9. Moreover, the detachably attached actuation unit 7 would provide intuitive maneuvering for the physician to complete the catheter attachment step, as well as the pre-insertion step for the orientation and position adjustment since the physician could hold and maneuver the catheter just like in conventional bronchoscopy.

On a third embodiment of the subject innovation, the actuation unit 7 is permanently attached to supporting insertion unit 9. The initial description of this third embodiment is identical to the second embodiment, with the workflow differing at the point where the Physician 10 inserts the bendable body 3.

Specifically, the difference of this third embodiment from the second embodiment is the detachably attached actuation unit 7. In this third embodiment, the actuation unit 7 would be mounted on the slider 101 permanently. The procedure associated with this third embodiment can be seen in FIG. 9A-9C, which depict the slider 101 affixed to the bendable body 3 (FIGS. 9B and 9C).

The remaining functional steps are interchangeable with those detailed in FIGS. 7A and 8A, and incorporated by reference in their entirely herein.

It is further contemplated in this third embodiment that the actuation unit 7 may be permanently mounted to the stage, wherein the handle and slider are one unit. Accordingly, the end user would then slide the actuation unit 7 and slider 15 (See FIG. 2A) combination down the base 16 manually until the catheter reaches the first target, then pick up the hand controller and the actuation unit 7/slider 15 combo would continue down the base 16 but would be controlled robotically, instead of manually.

While the present disclosure has been described with reference to exemplary embodiments, it is to be understood that the disclosure is not limited to the sample exemplary embodiments provided herein. The scope of the following claims is to be accorded the broadest interpretation so as to encompass all such modifications and equivalent structures and functions.

The invention claimed is:

1. A method comprising:
   providing a medical apparatus comprising:
   a bendable body including at least a first bendable section and a second bendable section;
   at least one control wire slideably situated in the bendable body and attached to a distal end of the bendable body;
   an actuator configured to actuate the at least one control wire to manipulate the first bendable section and/or the second bendable section;
   a supporting insertion unit configured to removably couple with the bendable body, for manual manipulation and/or robotic manipulation of the bendable body; and
   a controller:
   manually moving, by a user, the bendable body, with the bendable body not coupled to the supporting insertion unit;
   coupling the bendable body to the supporting insertion unit;
   manually manipulating, by the user, the medical apparatus, while the bendable body is coupled on the supporting insertion unit; and
   receiving, from the user, instructions to robotically manipulate the medical apparatus, while the bendable body is coupled to the supporting insertion unit,
   wherein the controller is configured to control the first bendable section directly associated with an input from the user, and to control the second bendable section associated with an algorithm in the controller.

2. The method of claim 1,
   wherein the controller is configured to control movement of the at least one control wire.

3. The method of claim 1,
   wherein the controller is configured to robotically manipulate the at least one control wire.

4. The method of claim 1,
   wherein the actuator is configured for the manual manipulation of the medical apparatus, when the medical apparatus is not coupled to the supporting insertion unit.

5. The method of claim 1,
   wherein the actuator is configured to be held by the user when the bendable body is not coupled to the supporting insertion unit.

6. The method of claim 1,
   wherein the supporting insertion unit comprises at least one force sensor configured to measure a force applied to the bendable body.

7. The method of claim 1, wherein, during the manual manipulation of the medical apparatus, the medical apparatus is coupled to and guided by the supporting insertion unit.

8. The method of claim 1, wherein the medical apparatus includes a tool channel extending along at least a part of a length of the bendable body of the medical apparatus.

9. The method of claim 8, wherein the tool channel is configured to accommodate a biopsy tool, a camera, or the like.

10. The medical apparatus of claim 1, wherein the tool channel is configured to accommodate a biopsy tool, a camera, or the like.

11. The method of claim 1, wherein the bendable body includes at least a third bendable section, and wherein, during the robotic manipulation, the controller is configured to control movement of the first bendable section, the second bendable section and/or the third bendable section via the actuator and the supporting insertion unit in a plurality of degrees of freedom.

12. A medical apparatus comprising:

a bendable body including at least a first bendable section and a second bendable section;

at least one control wire slideably situated in the bendable body and attached to a distal end of the bendable body;

an actuator configured to actuate the at least one control wire to manipulate the first bendable section and/or the second bendable section;

a supporting insertion unit configured to removably couple with the bendable body, for manual manipulation and/or robotic manipulation of the bendable body; and a controller, wherein, during the manual manipulation of the medical apparatus, the medical apparatus is supported by the supporting insertion unit, and

wherein the controller is configured to control the first bendable section directly associated with an input from the user, and to control the second bendable section associated with an algorithm in the controller.

13. The medical apparatus of claim 12, wherein the controller is further configured to manipulate the at least one control wire.

14. The medical apparatus of claim 12, wherein the controller is configured to robotically manipulate the at least one control wire.

15. The medical apparatus of claim 12, wherein the actuator is configured for the manual manipulation of the medical apparatus, when the medical apparatus is not coupled to the supporting insertion unit.

16. The medical apparatus of claim 12, wherein the actuator is configured to be held by a user when the bendable body is not coupled to the supporting insertion unit.

17. The medical apparatus of claim 12, wherein the supporting insertion unit comprises at least one force sensor configured to measure a force applied to the bendable body.

18. The medical apparatus of claim 12, further comprising a tool channel extending along at least a part of a length of the bendable body of the medical apparatus.

19. The medical apparatus of claim 12, wherein the bendable body includes a third bendable section, and wherein, during the robotic manipulation, the controller is configured to control movement of the first bendable section, the second bendable section and/or the third bendable section via the actuator and the supporting insertion unit in a plurality of degrees of freedom.

* * * * *